US008092440B2

(12) United States Patent
Hermansson et al.

(10) Patent No.: US 8,092,440 B2
(45) Date of Patent: Jan. 10, 2012

(54) ABSORBENT ARTICLE WITH IMPROVED LEAKAGE SECURITY AND FIT

(75) Inventors: Kent Hermansson, Västra Frölunda (SE); Carina Hedlund, Mölnlycke (SE); Niclas Norrby, Göteborg (SE); Jan Wästlund-Karlsson, Mölndal (SE); Margareta Wennerbäck, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 7 days.

(21) Appl. No.: 11/628,869

(22) PCT Filed: Jun. 28, 2004

(86) PCT No.: PCT/SE2004/001035
§ 371 (c)(1),
(2), (4) Date: Dec. 8, 2006

(87) PCT Pub. No.: WO2006/001737
PCT Pub. Date: Jan. 5, 2006

(65) Prior Publication Data
US 2007/0239131 A1 Oct. 11, 2007

(51) Int. Cl.
*A61F 13/15* (2006.01)
*A61F 13/20* (2006.01)
(52) U.S. Cl. ............... 604/385.27; 604/385.24
(58) Field of Classification Search ............ 604/385.22, 604/385.24–385.3, 392–396
See application file for complete search history.

(56) References Cited

U.S. PATENT DOCUMENTS

| 5,376,430 | A | | 12/1994 | Swenson et al. |
| 5,745,922 | A | * | 5/1998 | Rajala et al. ............... 2/243.1 |
| 5,807,368 | A | * | 9/1998 | Helmer ................. 604/373 |
| 6,098,203 | A | * | 8/2000 | Rajala et al. ................. 2/401 |
| 6,478,786 | B1 | * | 11/2002 | Glaug et al. ............ 604/385.27 |
| 6,602,238 | B2 | * | 8/2003 | Takei et al. ............ 604/385.26 |
| 6,620,146 | B2 | * | 9/2003 | Gibbs ................. 604/385.3 |
| 2002/0138065 | A1 | * | 9/2002 | Yeater et al. ............. 604/395 |
| 2002/0177829 | A1 | * | 11/2002 | Fell et al. ............. 604/385.01 |
| 2003/0139726 | A1 | * | 7/2003 | Gibbs ................ 604/385.29 |
| 2003/0171731 | A1 | * | 9/2003 | Johnston et al. ........ 604/385.27 |
| 2004/0186452 | A1 | | 9/2004 | Sandin et al. |
| 2004/0230171 | A1 | * | 11/2004 | Ando et al. .............. 604/355 |
| 2004/0243086 | A1 | | 12/2004 | VanGompel et al. |

(Continued)

FOREIGN PATENT DOCUMENTS
EP 1155668 A2 * 11/2001
(Continued)

OTHER PUBLICATIONS
Definition of "continuous", Merriam-Webster OnLine.*
(Continued)

*Primary Examiner* — Michele M Kidwell
(74) *Attorney, Agent, or Firm* — Buchanan Ingersoll & Rooney PC

(57) ABSTRACT

An absorbent article of the kind which is worn as a pair of absorbent pants with a waist opening defined by a rear waist edge and a front waist edge, and two leg openings. The absorbent article preferably includes an absorbent body attached to a covering. The covering preferably includes an elastic material arranged within an area which extends at least from the front waist edge to the leg openings. The elastic material is preferably treated. The treated elastic material preferably has no or reduced elasticity within a portion of the covering overlapping the absorbent core.

18 Claims, 4 Drawing Sheets

U.S. PATENT DOCUMENTS

2004/0267218 A1   12/2004   Sandin et al.

FOREIGN PATENT DOCUMENTS

| | | |
|---|---|---|
| EP | 1300124 A2 * | 4/2003 |
| JP | 7-508473 T | 9/1995 |
| JP | 9-286085 A | 11/1997 |
| JP | 2002-035029 A | 2/2002 |
| JP | 2002-102282 A | 4/2002 |
| JP | 2002-272784 A | 9/2002 |
| WO | WO 94/00292 A1 | 1/1994 |
| WO | WO 02/074213 A1 | 9/2002 |
| WO | 03/070141 A1 | 8/2003 |
| WO | 2004/078084 A1 | 9/2004 |

OTHER PUBLICATIONS

PCT/ISA/210.
PCT/ISA/237.
International Preliminary Report on Patentability issued in PCT/SE2004/001035 on Dec. 28, 2006, The International Bureau of WIPO Geneva, CH; and attached Written Opinion.
Notice of Reasons for Rejection issued in the corresponding Japanese patent application No. 2007-517996 on Jan. 26, 2010.
English-language translation of a Japanese Official Inquiry dated Feb. 8, 2011 issued in corresponding Japanese Patent Application No. 2007-517996.

* cited by examiner

ABSORBENT ARTICLE WITH IMPROVED LEAKAGE SECURITY AND FIT

TECHNICAL FIELD

The invention relates to an absorbent article of the kind which is worn as a pair of absorbent pants with a waist opening defined by a rear waist edge and a front waist edge, and two leg openings, and comprising an absorbent body attached to a covering, the covering comprising an elastic material arranged within an area which extends at least from the front waist edge to the leg openings.

BACKGROUND ART

Absorbent articles such as diapers, sanitary towels and incontinence pads are intended to catch and absorb body discharges of various kinds. In this connection, demands are made for the absorbent articles to be designed in such a way that reliable and adequate leakage security and absorption capacity are provided. For adult users, it is moreover important that the articles are discreet and can be worn without being noticed under normal clothes and are also comfortable to wear.

One difficulty associated with the design of an absorbent article intended to be worn in the crotch area of a user is that the space, and thus the area over which the absorbent body of the absorbent article can extend, is limited. There is therefore an obvious risk of that area of the article which is affected first by body discharge becoming saturated and being incapable of further absorption when the next discharge takes place. In order to prevent leakage past the side edges on an absorbent article of this kind, it is therefore common to provide the article with some type of edge barrier. Such edge barriers are in most cases elastic and can form raised physical obstacles to the flow of discharges emitted. On diapers and incontinence pads of the kind worn as a pair of absorbent pants, it is usual to arrange elastic elements which tighten around the legs of the user and in this way keep the edges of the article in sealing contact with the legs.

In order to ensure a high degree of leakage security, the absorbent articles must also be designed so that they fit the body of the user closely in such a way that the absorbent articles do not become loose or slip off the body of the wearer. The covering layers which constitute a major part of the absorbent articles are therefore usually provided with a number of elastic threads arranged parallel from the waist opening down towards the leg openings and over part of the absorbent core. In this connection, the absorbent articles are provided with a fit so that both good leakage security and a close fit are obtained. These advantages are also most advantageously achieved with absorbent articles which are made from ready-elastic materials such as elastic non-wovens or elastic laminates.

Even if the absorbent articles have a closer fit against the body, another problem arises in that that part of the absorbent core which is covered by the elastic threads will be puckered, which results in a risk of the absorbent material comprised in the absorbent core being folded together or alternatively pulled apart. Owing to this, channels may be formed in the absorbent material, which, for example when a discharge of urine takes place, are filled with liquid in such a way that the elastic elements around the legs and/or the edge barriers are unable to counteract the liquid flow produced. In such a situation, there is a risk of the liquid conveyed in the channels being conducted out of the absorbent articles, and of the other clean body surfaces and garments of the user being soiled.

This problem can be solved by allowing the elastic threads, or the elastic material, to extend over only the upper portions of the absorbent articles next to the waist opening and not over the absorbent core. However, the problem then arises that those parts of the absorbent articles located on each side of the absorbent core are left unelasticated and the closer fit desired for on the one hand reasons of leakage security and on the other hand aesthetic reasons is lost.

As emerges from the above, there is a need for absorbent articles which have such a good fit that they are discreet and flexible to wear and that they fit the body of the user closely and prevent leakage. Additionally, there is a need for a simple and cost-effective method for manufacturing said absorbent articles.

OBJECTS AND SUMMARY

In accordance with embodiments of the invention, an absorbent article of the kind which is worn as a pair of absorbent pants and comprising an absorbent body attached to a covering, the covering comprising an elastic material, has now been produced. An absorbent article according to embodiments of the invention is characterized mainly in that the elastic material has been treated within a portion of the covering overlapping the absorbent core and by virtue of this has no or reduced elasticity within the treated portion.

For example, a pants absorbent article according to one embodiment includes a waist opening defined by a rear waist edge formed on a rear portion and a front waist edge formed on a front portion, and two leg openings. The article also includes an absorbent body attached to a covering. The covering comprises an elastic material arranged continuously at least from the front waist edge of the front portion to the leg openings and extending continuously from one side edge of the front portion to another side edge of the front portion except that a portion of the elastic material which remains within a portion of the covering overlapping the absorbent core in the front portion has been treated, such that the treated portion of elastic material which remains within the portion of the covering has reduced elasticity.

The reduction in elasticity can be expressed as a reduction of the force the material exerts when it contracts after extension. This force is called the return force and is at least 50% lower in the treated portion of the elastic material than in the untreated elastic material.

Embodiments of the invention provide the absorbent pants with an optimum combination of elasticity and fit with minimal negative effect on the absorbent core of the article.

According to one embodiment of the invention, the covering comprises an elastic material within an area which extends at least from the rear waist edge to the leg openings. An elastic material is therefore arranged as a trunk-enclosing band or belt extending over both the front portion of the article and its rear portion.

The pants-like absorbent article can be divided into a front portion, a rear portion and an intermediate crotch portion. In this connection, the front portion is that part of the article which is intended to be arranged over the abdomen of the user during use, the rear portion is the part which is arranged over the seat of the wearer during use, and the crotch portion is that part of the article which is arranged in the crotch of the wearer. There are no clear boundaries between the various portions of the article, but each portion usually takes up approximately a third of the length of the article even though the size may vary slightly depending on the design of the article. For example, the rear portion may be slightly longer than the front portion, the crotch portion then being shifted forwards on the article.

According to one embodiment of the invention, the elastic material can be arranged over both the front portion and the rear portion and the crotch portion. It is then preferred if the elastic material is treated over at least that part of the part of the covering overlapping the absorbent core which is located in the crotch portion. This is because it is this part of the absorbent core which is first subjected to wetting during use and which is thus most susceptible to mechanical influence and deformation.

In order to bring about sufficient de-elastication of the crotch portion, it is suitable if at least 30% and preferably at least 70% of that part of the covering overlapping the absorbent core is treated so that the elastic material is essentially de-elasticated.

In order to have as little effect as possible on the absorbent core, the elastic material can be treated over the whole of that part of the covering overlapping the absorbent core, so that only those parts of the elastic material located outside the periphery of the absorbent core retain their full elasticity.

The treatment of the elastic material can be carried out using heat, ultrasound, chemical agents, freezing or cutting and results in the elasticity in the material being eliminated ("killed") or at least reduced so considerably that it is incapable of puckering or otherwise deforming the absorbent core.

The elastic material included in the covering can be one or more layer(s) of elastic non-woven.

Another suitable material for use in the covering is one or more layer(s) of elastic laminate, for example a laminate of non-woven and elastic film.

The covering can also be elasticated by virtue of comprising a plurality of elastic elements. Such elastic elements can suitably be essentially parallel elastic threads or bands applied to a carrier layer of non-woven or the like. It may also be suitable to apply the elastic elements between two material layers. In order to achieve sufficient elastication of the elasticated area, the elastic elements should be placed at a mutual distance of at most 40 mm and preferably at a mutual distance of at most 20 mm. Furthermore, at least 5 essentially parallel elastic elements should be arranged within the elasticated area.

BRIEF DESCRIPTION OF FIGURES

Embodiments of the invention will be described in greater detail below with reference to the embodiments shown in the accompanying drawings, in which.

DESCRIPTION OF ILLUSTRATIVE EMBODIMENTS

Figure 1:
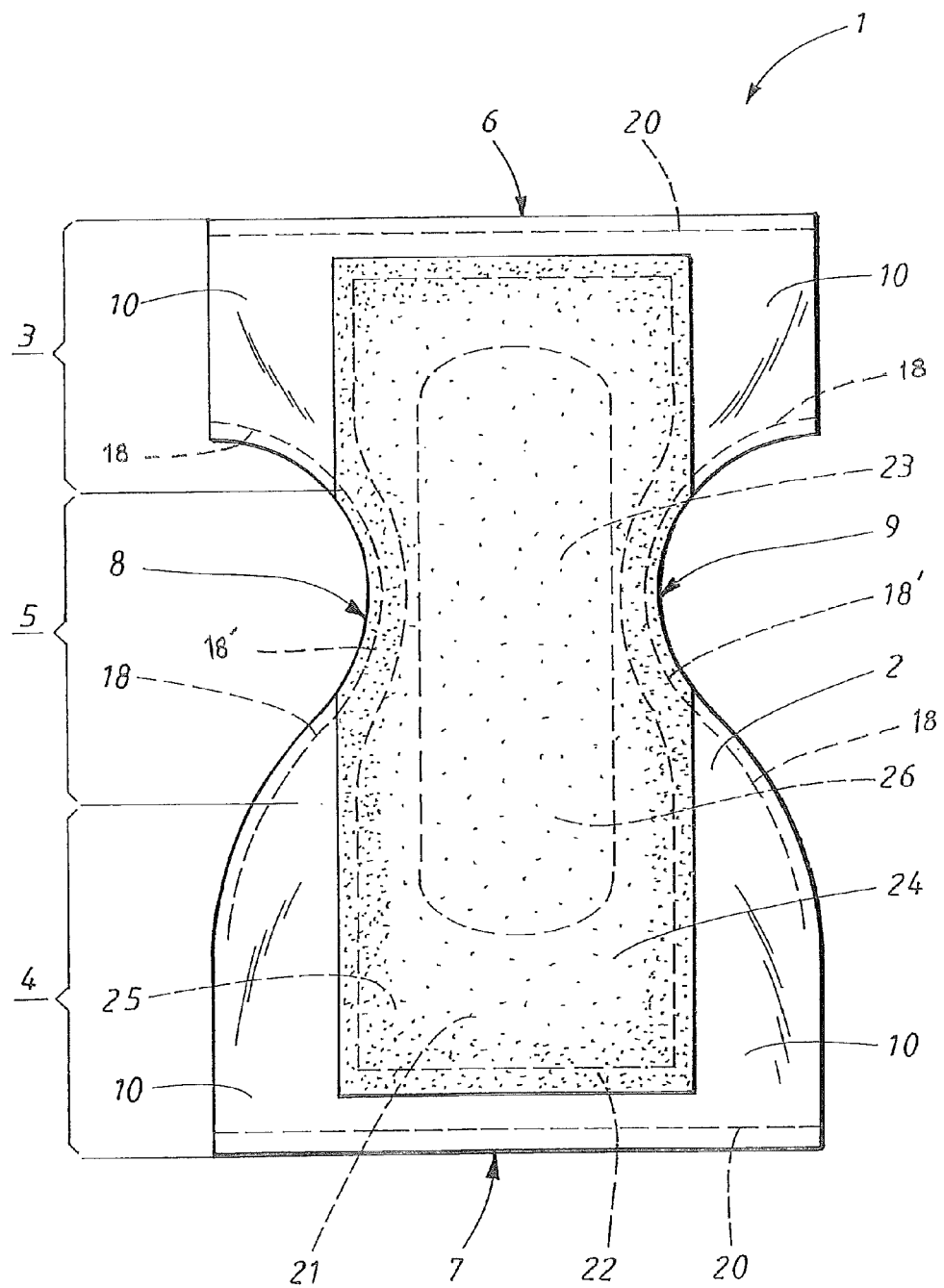
FIG. 1 shows a pant diaper according to a first embodiment of the invention, seen in a plane, stretched-out state before joining together in the form of pants.
Figure 2:
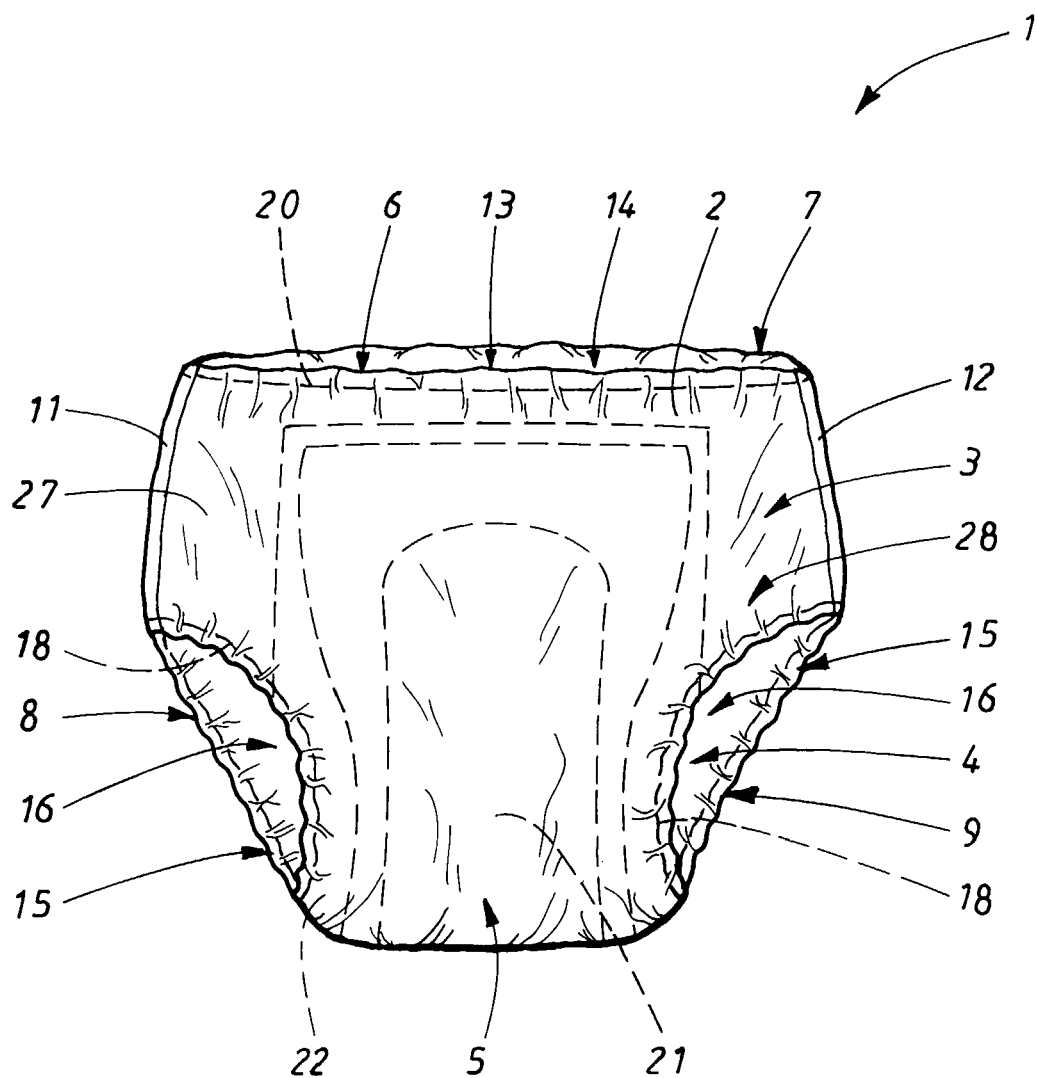
FIG. 2 shows the pant diaper in FIG. 1 as it appears when joined together in the form of pants.

For the sake of clarity, the pant diaper 1 in FIG. 1 is shown in a not fully joined-together, plane, stretched-out state and is seen from the side which faces the wearer when the pant diaper is worn. FIG. 2 shows the pant diaper 1 as it appears in joined-together form and without being subjected to extending forces. The pant diaper comprises outer pants 2 which can be divided into a front portion 3, which is intended to face forwards on the user and to be arranged over the abdomen of the wearer during use, a rear portion 4, which is intended to face backwards on the user and to be arranged over the buttocks of the user during use, and a crotch portion 5 located between the front portion 3 and the rear portion 4, which is intended to be arranged in the crotch of the user during use.

In the stretched-out state shown in FIG. 1, the pant diaper 1 has a straight front end edge or front edge 6 extending in the transverse direction of the pant diaper, a straight rear end edge or rear edge 7 extending in the transverse direction, and two side edges 8, 9 extending mainly in the longitudinal direction, which each have a front and a rear essentially straight portion and an intermediate curved portion.

In the joined-together state, as shown in FIG. 2, the front portion of each side edge 8, 9 is joined together with the corresponding rear portion in a side join 11, 12. In this way, the front edge 6 and the rear edge 7 form a waist edge 13 which surrounds a waist opening 14, and the curved portions of the side edges 8, 9 form leg edges 15 which surround leg openings 16.

The side joins 11, 12 are suitably but not necessarily made in such a way that they can withstand the tensile forces which arise when the pant diaper is put on and used but so that they can be torn apart when the used absorbent pants are taken off. An openable side join 12 therefore only has sufficient holding-together capacity that the join breaks at a lower force than is required to pull the surrounding material of the pant diaper apart.

The side joins 11, 12 can be made by, for example, welding or gluing.

The outer pants 2 comprise a layer of an elastic material such as an elastic non-woven material or an elastic film. An elastic non-woven material which is suitable for use in absorbent pants in accordance with embodiments of the invention should be capable of being extended elastically by at least 50% and preferably at least 80% in the transverse direction of the pants in order to obtain a good fit of the pants. It is also advantageous if the elastic non-woven material can also be extended elastically in the longitudinal direction of the absorbent pants, that is to say in a direction at right angles to the transverse direction.

The elastic layer material included in the outer pants 2 can comprise a laminate of two or more layers. A material suitable for the purpose is a three-layer laminate with a non-woven layer on each side of a perforated elastic film. Such a laminate provides elastic and breathable outer pants. It is also possible to use other, preferably breathable, elastic materials. For example, what are known as elastic SMS materials can be used. An SMS material is a non-woven laminate with a layer of spunbond non-woven on each side of a meltblown non-woven layer. In such a laminate, the meltblown layer then includes elastic elements in the form of elastic fibres.

Separate elastic elements are arranged as leg elastic 18 around the leg openings 16 and as waist elastic 20 around the waist opening 14. When the outer pants 2 are made from a laminate of two or more layers, the elastic elements 18, 20 are suitably fixed between two such layers. An alternative for obtaining increased elastic effect around the waist opening 14 is to fold the elastic material in the outer pants 2, so that a band edge with increased stretch resistance is formed around the waist opening 14.

The elastic elements in the leg elastic 18 and the waist elastic 20 can be in the form of elastic threads, bands or the like. If elastic threads or bands are used, two or more of these are often applied parallel to one another and then constitute elastic part elements in the elastic element. The material can be rubber, elastic foam, etc.

A core pack 21 is fixed inside the elastically stretchable outer pants 2, for example by means of adhesive or welding. The core pack 21 can be fixed to the outer pants 2 over the whole of the common surface or over only parts of it. The core pack 21 should, however, be sufficiently well fixed inside the outer pants 2 to avoid it coming loose or being shifted out of position during use.

The core pack 21 comprises a liquid barrier layer 22, an absorbent core 23 and a liquid-permeable inner layer 24. The core pack 21 is fixed to the outer pants 2 by the liquid barrier layer 22. FIG. 1 shows an absorbent core 23 comprising two absorbent layers 25, 26 laid one on another, the lower absorbent layer 25 located next to the liquid barrier layer 22 being slightly larger than the upper absorbent layer 26 located next to the inner layer 24. In the example shown, the core pack 21 has an angular hourglass shape in the plane, the plane shape of the core pack being defined by the shape of the liquid barrier layer 22 and the liquid-permeable inner layer 24, which together enclose the absorbent core 23. It is of course possible to use core packs 21 with a different plane shape; for example, the liquid barrier layer 22 and the inner layer 24 can have a more rounded hourglass shape, a rectangular shape, a trapezoidal shape, an oval shape etc. The core pack 21 does not have to have the size shown in the figure either. Both larger and smaller absorbent bodies 23 can be used, depending on the absorption capacity desired for the pant diaper.

The liquid-permeable inner layer 24 can comprise any material known for the purpose, such as a layer of non-woven material, perforated plastic film, net material, tow or the like. The inner layer 24 can of course also comprise a laminate of two or more layers of the same material or different materials.

The liquid barrier layer 22 can comprise a liquid-impermeable plastic film, a hydrophobic non-woven layer or a non-woven layer which has been treated so as to take on liquid barrier properties, or another flexible material layer capable of resisting liquid penetration. It may be an advantage, however, if the liquid barrier layer 22 has a certain breathability, that is to say allows water vapour to pass through the layer 22.

The absorbent core 23 can be constructed from absorbent material, such as cellulose fluff pulp, tissue, absorbent foam etc. It is also common for the absorbent core 23 to contain superabsorbents, that is to say polymer materials which can absorb body fluid corresponding to several times their own weight while forming a hydrogel. Such superabsorbents are usually present in the form of particles, but fibres, flakes, granules and film are also found. The absorbent core 23 can also comprise non-absorbent components such as stiffening elements, shaping elements, binders etc. Various types of liquid-receiving and liquid-distributing structures such as fibre wadding, open-cell foam, spreading layers or the like can also form part of the core pack 21.

The various components included in the core pack 21 can be interconnected in a conventional way, for example by gluing or welding using heat or ultrasound. The core pack 21 can of course contain other components apart from those described here; for example, the core pack can comprise liquid-transport layers, elastic elements, shape-stabilizing means, shaping elements or the like. Although the absorbent body has been shown with two absorbent layers 25, 26, alternative embodiments can be used. For example, a single absorbent layer may be sufficient for some applications, while other applications may require more than two absorbent layers. The design of the absorbent core can therefore be adapted to the quantity of liquid the absorbent core is expected to absorb. Of course, the type of body discharges to be absorbed and the way in which the body discharges are delivered to the absorbent core are also of significance for the size and nature of the absorbent core.

The elastic elements 18 along the edges of the absorbent core 23 can either constitute components of the core pack and be applied together with it or be applied to the outer pants 2.

As mentioned above, elastically contracting forces can have a negative deforming effect on the relatively rigid material of the absorbent core 23, so that folds and irregularities are formed, in which liquid can accumulate and be conducted out of the pant diaper. In order to avoid this, the elastic material 18' in the outer pants 2 has been treated within the area where the absorbent core 23 is positioned, so that the elastic properties of the material are greatly reduced or eliminated. Such treatment can be carried out by means of, for example, heating the material within the area concerned, or chemically. Alternatively, ultrasound, freezing or cutting can be used. The treatment can be carried out on the elastic material 18' before it is introduced into a manufacturing process for production of the pant diaper. Alternatively, the treatment can be included as a process step during production of the pant diaper, or as a finishing step for the joined-together pant diaper. It is not necessary for the whole of the area which constitutes the interface between the absorbent core 23 and the outer pants 2 to be treated. However, it is particularly suitable if at least that part of the interface which is located in the crotch portion 5 is treated, as the crotch portion 5 is that part of the pant diaper 1 which is expected to receive and absorb discharged body fluid first for onward spreading to other parts of the absorbent core 23. Therefore, at least 30% of the interface and preferably at least 70% should be treated so that the elastic material is essentially de-elasticated.

As only portions coinciding with the extent of the absorbent core 23 on the outer pants 2 have been treated so as to de-elasticate the elastic material. Thus, the elasticity remains unchanged in the portions 10 of the outer pants 2 which extend outside the absorbent core 23. In the joined-together pant diaper 1, these portions 10 form elastic side panels 27, 28 which ensure a good tight fit of the pant diaper over the hips of the user during use of the pant diaper.

As mentioned above, FIG. 2 shows how the pant diaper looks before it is put on. All elastic elements and components are essentially unextended. As the leg elastic 18 and the waist elastic 20 are fixed to the outer pants 2 in an extended state, they contract the material of the outer pants 2 when the tensioning ceases. This means that, before it is put on, the pant diaper 1 has a slightly puckered waist edge 13 and leg edges 15 which are puckered on the crotch portion 5 and the rear portion 4.

Figure 3:
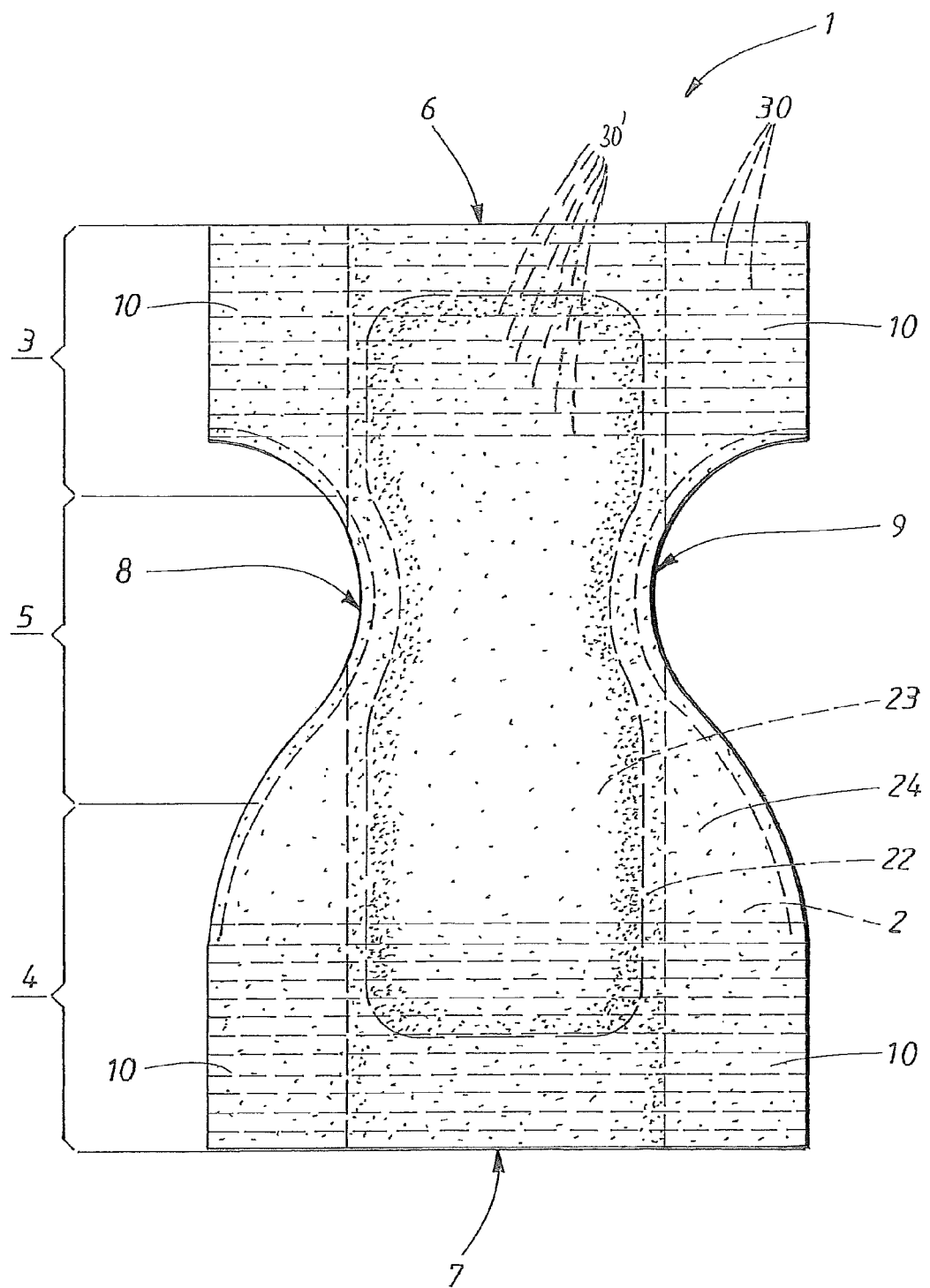
FIG. 3 shows a pant diaper according to a second embodiment of the invention, seen in a plane, stretched-out state before joining together in the form of pants.
Figure 4:
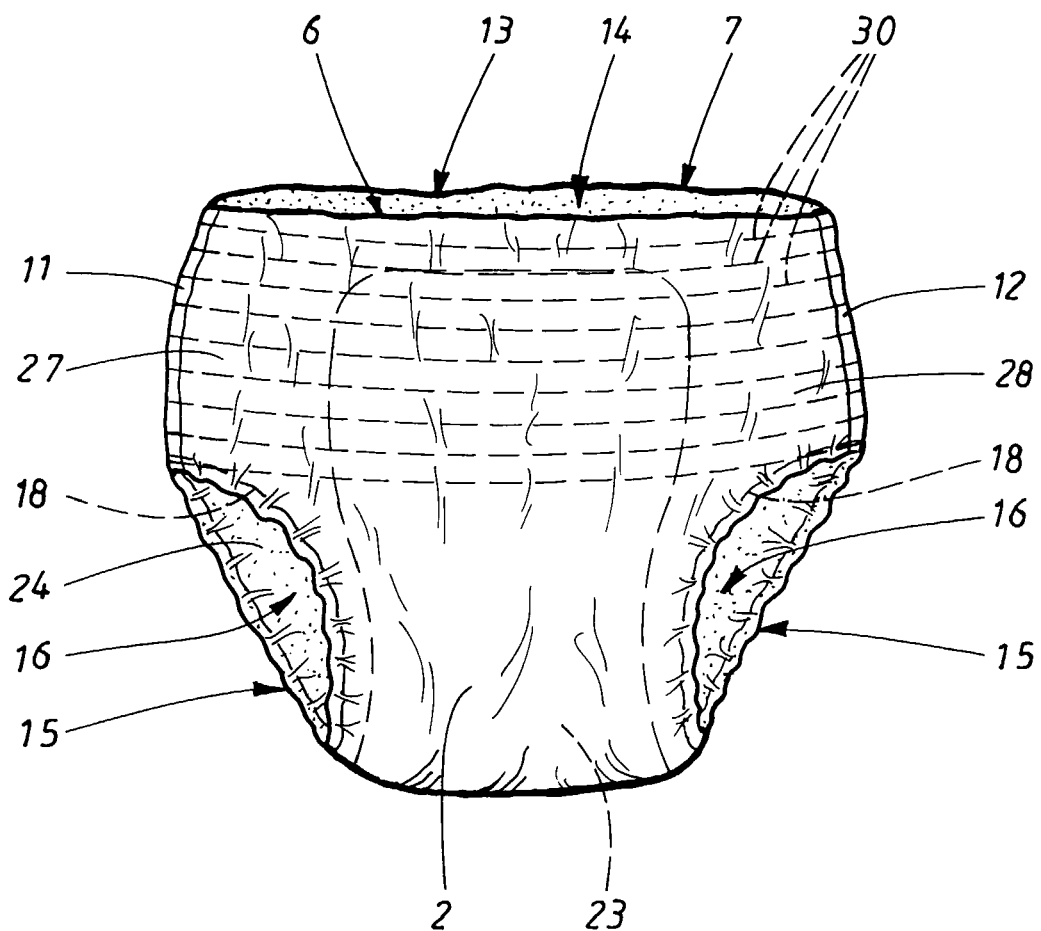
FIG. 4 shows the pant diaper in FIG. 3 as it appears when joined together in the form of pants.

The pant diaper shown in FIGS. 3 and 4 has a slightly different construction from the pant diaper in FIGS. 1 and 2. However, corresponding components have been assigned the same reference numbers.

In the same way as in the pant diaper described above, the pant diaper in FIG. 3 is shown in a not fully joined-together, plane, stretched-out state and is seen from the side which faces the wearer when the pant diaper is worn. FIG. 4 shows the pant diaper 1 as it appears in joined-together form and without being subjected to extending forces.

The pant diaper can be divided into a front portion 3, which is intended to face forwards on the user and to be arranged over the abdomen of the user during use, a rear portion 4, which is intended to face backwards on the user and to be arranged over the buttocks of the user during use, and a narrower crotch portion 5 located between the front portion 3 and the rear portion 4, which is intended to be arranged in the crotch of the user during use.

In the stretched-out state shown in FIG. 3, the pant diaper 1 has a straight front end edge or front edge 6, a straight rear end edge or rear edge 7 and two side edges 8, 9 which each have a front and a rear essentially straight portion and an intermediate curved portion.

In the joined-together state, as shown in FIG. 4, the front portion of each side edge 8, 9 is joined together with the corresponding rear portion in a side join 11, 12, as described above in connection with the pant diaper shown in FIGS. 1 and 2. In this way, the front edge 6 and the rear edge 7 form a waist edge 13 which surrounds a waist opening 14, and the curved portions of the side edges 8, 9 form leg edges 15 which surround leg openings 16.

The pant diaper 1 comprises an outer covering layer 2 made of a thin flexible material, preferably a non-woven material which provides a textile outer surface on the pant diaper. The outer covering layer 2 can, however, be any flexible material suitable for the purpose such as various types of laminate, plastic film or the like. It is preferred that the outer covering layer 2 is breathable, at least within those areas where a liquid barrier is not required. If a plastic film is used, this can therefore suitably be perforated within the areas where the barrier properties of the film are not required.

Separate elastic elements are arranged as leg elastic 18 around the leg openings 16. Moreover, a number of elastic elements 30 are arranged parallel to the end edges 6, 7, between each end edge 6, 7 and up to the leg openings 16. In the example shown, the elastic elements 30 are arranged at a uniform distance from one another and are distributed over the whole area between the waist edge 13 of the pant diaper 1 and the upper part of the leg openings in such a way that the whole of this area can be regarded as being provided with elastic elements 30. In order to bring about sufficient elastication of an area such as that shown in FIGS. 3 and 4, it is normally necessary for at least 5 elastic threads or bands to be distributed over the area with one elastic element 30 close to the waist opening 14, one close to the leg openings 16 and the other elements 30 distributed in between. It is not necessary for the distance between the elastic elements 30 to be entirely uniform, but, in order for it to be possible for the area provided with elastic to be regarded as being elasticated, at least for the embodiments of the present invention, the distance between the elastic elements 30 should not exceed 4 cm and preferably the distance between the elastic elements 30 should not exceed 2 cm.

The elastic elements in the leg elastic 18 and the elastic elements 30 on the front portion 3 and rear portion 4 of the pant diaper can be in the form of elastic threads, bands or the like. At the waist edge 13, the waist elastic can be reinforced by the elastic elements 30 being arranged closer together immediately next to the edge, by the edge being doubled or by arranging a special waist elastic element next to the waist edge 13.

The pant diaper 1 shown in FIGS. 3 and 4 comprises a liquid barrier layer 22, an absorbent core 23 and a liquid-permeable inner layer 24. The absorbent core is fixed to the liquid barrier layer 22 which in turn is fixed to the outer covering layer 2. If the outer covering layer 2 is a liquid-impermeable layer, a separate liquid barrier layer is of course not required.

The liquid barrier layer 22 can comprise a liquidtight plastic film, a hydrophobic non-woven layer or a non-woven layer which has been treated so as to take on liquid-blocking properties, or another flexible material layer capable of resisting liquid penetration. It may be an advantage, however, if the liquid barrier layer 22 has a certain breathability, that is to say allows water vapour to pass through the layer 22.

The liquid-permeable inner layer 24 can comprise any material known for the purpose, such as a layer of non-woven material, perforated plastic film, net material, tow or the like. The inner layer 24 can of course also comprise a laminate of two or more layers of the same material or different materials.

The absorbent core 23 can be constructed from absorbent material, such as cellulose fluff pulp, tissue, absorbent foam etc. It is also common for the absorbent core 23 to contain superabsorbents, that is to say polymer materials which can absorb body fluid corresponding to several times their own weight while forming a hydrogel. Such superabsorbents are usually present in the form of particles, but fibres, flakes, granules and film are also found. The absorbent core 23 can also comprise non-absorbent components such as stiffening elements, shaping elements, binders etc. Various types of liquid-receiving and liquid-distributing structures such as fibre wadding, open-cell foam, spreading layers or the like can also be arranged between the absorbent core 23 and the liquid-permeable inner layer 24.

The absorbent core 23 is therefore enclosed between the liquid-permeable inner layer 24 and the outer covering layer 2. The elastic elements 18, 30 can be fixed to either or both of these layers 24, 2. It is also possible to fix the elastic elements 30 extending in the transverse direction of the pant diaper between two layers in a laminate which forms part of the outer covering layer 2 or the inner layer 24.

In accordance with embodiments of the invention, the elastic elements 30 have been treated 30' within the area where the absorbent core 23 is positioned, so that the elastic properties of the elastic elements 30' have been greatly reduced or eliminated. As mentioned above, such treatment can be carried out by means of, for example, heating the material within the area concerned, or chemically.

Only portions 30' coinciding with the extent of the absorbent core 23 on the outer covering layer 2 have been treated so as to de-elasticate the elastic elements 30. Thus, the elasticity remains unchanged in the portions 10 of the covering 2, 24 which extend outside the absorbent core 23. In the joined-together pant diaper 1, these portions 10 form elastic side panels 27, 28 which ensure a good tight fit of the pant diaper over the hips of the user during use of the pant diaper.

Although embodiments of the invention have been described in connection with pant diapers, it is of course possible to apply it to other types of absorbent article which are worn as a pair of pants as well. Such absorbent articles include absorbent menstruation pants and all-in-one diapers, that is to say diapers which are fastened together in the form of pants in connection with being put on.

In order to determine the elasticity of an elastic material, use can be made of a test in which the behaviour of the material after repeated cycles of loading and relaxation is measured. A specimen is fixed between two clamps and is stretched to a predetermined extension, and cyclic shifting between 0 and the predetermined extension is carried out. Permanent, that is to say remaining, elongation of the relaxed material is measured.

The test is carried out in a known way using a tensile tester provided with a printer or other presentation equipment. The specimen is prepared by cutting out a width of 25 mm and a length which is suitably 20 mm longer than the distance between the clamps in the tensile tester. The test is carried out with an initial stress of 0.05 N.

The tensile tester is calibrated in accordance with the instructions for the apparatus, and measurement is performed at a rate of 500 mm/minute and with a distance between the clamps of 50 mm.

The specimen is placed in the clamps, and it is ensured that the specimen is centred and fixed at right angles in the clamps. The tensile tester is started, and three cycles between 0 and the predetermined extension are carried out. Before the last cycle, the specimen is relaxed for 1 minute, after which the permanent deformation is measured by stretching the specimen until a force of 0.1 N is measured, the extension then being measured.

The permanent extension after relaxation of an elastic material with 30% elasticity is to be less than 10% when the material has been extended by 30% according to the method indicated above. An extension of 30% means that the material has been stretched to a length which is 30% greater than the initial specimen length.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. A pants absorbent article comprising a waist opening defined by a rear waist edge formed on a rear portion and a front waist edge formed on a front portion, and two leg openings, the article comprising an absorbent body attached to a covering,
    the covering comprising an elastic material, the elastic material comprising a plurality of elastic members arranged continuously at equal distances from each other at least from the front waist edge of the front portion to the leg openings and extending continuously from one side edge of the front portion to another side edge of the front portion, except that a portion of the elastic material which remains within a portion of the covering overlapping the absorbent core in the front portion has been treated, such that the treated portion of elastic material which remains within the portion of the covering has reduced elasticity.

2. The pants absorbent article according to claim 1, wherein the treated portion of elastic material has no elasticity.

3. The pants absorbent article according to claim 1, wherein the covering comprises an elastic material arranged within an area which extends at least from the rear waist edge to the leg openings.

4. The pants absorbent article according to claim 1, wherein the article also includes an intermediate crotch portion between the front portion and the rear portion,
    wherein the elastic material is further arranged over the rear portion and the crotch portion, and
    wherein a portion of the elastic material has been treated within a portion of the covering overlapping the absorbent core in the crotch portion.

5. The pants absorbent article according to claim 4, wherein at least 30% of the portion of the elastic material within the covering overlapping the absorbent core in the crotch portion has been treated,
    wherein the treated elastic material is essentially de-elasticated.

6. The pants absorbent article according to claim 4, wherein at least 70% of the portion of the elastic material within the covering overlapping the absorbent core in the crotch portion has been treated,
    wherein the treated elastic material is essentially de-elasticated.

7. The pants absorbent article according to claim 1, wherein the elastic material has been treated over the whole of the portion of the elastic material within the covering overlapping the absorbent core.

8. The pants absorbent article according to claim 1, wherein the treatment is selected from the group consisting of heat, ultrasound, chemical agents, freezing and cutting.

9. The pants absorbent article according to claim 1, wherein the covering comprises at least one layer of elastic non-woven.

10. The pants absorbent article according to claim 1, wherein the covering comprises at least one layer of elastic laminate.

11. The pants absorbent article according to claim 10, wherein the elastic laminate comprises an elastic film.

12. The pants absorbent article according to claim 1, wherein the elastic elements are between two material layers.

13. The pants absorbent article according to claim 12, wherein the elastic elements comprise essentially parallel elastic bands or threads at a mutual distance not exceeding 40 mm.

14. The pants absorbent article according to claim 12, wherein the elastic elements comprise essentially parallel elastic bands or threads at a mutual distance not exceeding 20 mm.

15. The pants absorbent article according to claim 1, wherein the elasticity is reduced by at least 50% in the treated portion.

16. A pants absorbent article comprising a waist opening defined by a rear waist edge at a rear portion and a front waist edge at a front portion, and two leg openings, the article comprising an absorbent body attached to a covering,
    the covering comprising at least one single elastic material, the single elastic material arranged continuously without interruption at least from the front portion, extending through a crotch portion and to the rear portion, except that a portion of the single elastic material which remains within a portion of the covering overlapping the absorbent core has been treated, such that the treated portion of single elastic material which remains within the portion of the covering has reduced elasticity.

17. The pants absorbent article according to claim 16, wherein the elastic material is arranged at a side edge of the front portion.

18. A pants absorbent article comprising a waist opening defined by a rear waist edge formed on a rear portion and a front waist edge formed on a front portion, and two leg openings, the article comprising an absorbent body attached to a covering,
    the covering comprising an elastic material, the elastic material comprising a plurality of elastic members arranged at equal distances from each other to extend at least from the front waist edge of the front portion to the leg openings and through a longitudinal centerline of the article in a portion of the covering overlapping the absorbent core in the front portion, and to extend from one side edge of the front portion to another side edge of the front portion and through the longitudinal centerline in the portion of the covering overlapping the absorbent core,
    and a portion of the elastic material which remains within the portion of the covering overlapping the absorbent core in the front portion and extending through the longitudinal centerline of the article has been treated such that the treated portion of elastic material which remains within the portion of the covering has reduced elasticity.

* * * * *